US008919554B2

(12) United States Patent
Huldin

(10) Patent No.: US 8,919,554 B2
(45) Date of Patent: Dec. 30, 2014

(54) SPLASH-RETARDING FLUID COLLECTION SYSTEM

(75) Inventor: Nelson L. Huldin, Lake Barrington, IL (US)

(73) Assignee: Medline Industries, Inc., Mundelein, IL (US)

( * ) Notice: Subject to any disclaimer, the term of this patent is extended or adjusted under 35 U.S.C. 154(b) by 321 days.

(21) Appl. No.: 13/283,421

(22) Filed: Oct. 27, 2011

(65) Prior Publication Data

US 2013/0104989 A1   May 2, 2013

(51) Int. Cl.
*B65D 83/10* (2006.01)
*A61B 19/02* (2006.01)
*B65D 51/00* (2006.01)
*A61B 19/00* (2006.01)

(52) U.S. Cl.
CPC ............ *A61B 19/0287* (2013.01); *B65D 51/00* (2013.01); *A61B 19/42* (2013.01)
USPC ........................................................ 206/366

(58) Field of Classification Search
CPC .......... A61B 19/0287; A61B 19/0288; A61M 5/3205
USPC ........ 206/363–370; 110/238; 220/908, 908.1, 220/908.3; 141/86, 311 A; 604/110, 192
See application file for complete search history.

(56) References Cited

U.S. PATENT DOCUMENTS

| 2,511,682 | A | | 6/1950 | Russell | |
|---|---|---|---|---|---|
| 4,091,956 | A | | 5/1978 | Vecchio | |
| 4,936,449 | A | * | 6/1990 | Conard et al. | 206/366 |
| 5,024,343 | A | | 6/1991 | Lemelson | |
| 5,047,271 | A | | 9/1991 | Feddersen et al. | |
| 5,305,911 | A | | 4/1994 | Aylward | |
| 5,350,079 | A | * | 9/1994 | Larson et al. | 220/908 |
| 5,477,897 | A | | 12/1995 | Scofield | |
| 5,483,999 | A | | 1/1996 | Lampropoulos et al. | |
| 5,497,892 | A | | 3/1996 | Takatsuki | |
| 5,707,173 | A | * | 1/1998 | Cottone et al. | 206/366 |
| 5,769,223 | A | * | 6/1998 | Marsh | 206/365 |
| 5,887,739 | A | | 3/1999 | Prevot et al. | |

(Continued)

FOREIGN PATENT DOCUMENTS

| JP | 2004-067214 | 3/2004 |
|---|---|---|
| JP | 2006-123938 | 5/2006 |
| JP | 2009-280284 | 12/2009 |
| JP | 2011-073701 | 4/2011 |

OTHER PUBLICATIONS

Choi, Hyun G., "PCT Search Report and Written Opinion", PCT/US2013/050708; Filed Jul. 16, 2013; Mailed Oct. 7, 2013.

(Continued)

*Primary Examiner* — Luan K Bui
(74) *Attorney, Agent, or Firm* — David Noskowicz; Philip H. Burrus, IV

(57) ABSTRACT

A fluid collection container (100) includes a vessel (101) and a lid (102). A mesh conduit layer (201) is coupled to the vessel so as to span an opening (110) of the vessel and enclose an interior (111) of the vessel. The mesh conduit layer is liquid permeable and serves as a splash retarding mechanism that prevents liquids being transferred through the mesh conduit layer from splashing back. An optional cache (603) of coagulant material can be disposed within an interior of the vessel as well.

16 Claims, 9 Drawing Sheets

(56) References Cited

U.S. PATENT DOCUMENTS

| | | | | |
|---|---|---|---|---|
| 5,967,778 | A * | 10/1999 | Riitano | 206/366 |
| 6,053,314 | A * | 4/2000 | Pittman | 206/366 |
| 6,629,602 | B1 * | 10/2003 | Heyman | 206/366 |
| 6,681,925 | B2 * | 1/2004 | Fischer et al. | 206/369 |
| 6,719,017 | B1 | 4/2004 | McArthur et al. | |
| D502,993 | S | 3/2005 | McArthur et al. | |
| 7,174,928 | B1 | 2/2007 | Lampropoulos | |
| 7,225,927 | B2 | 6/2007 | Sweeney | |
| 7,458,463 | B2 | 12/2008 | Lampropoulos | |
| 7,507,062 | B2 | 3/2009 | Pasty | |
| 7,597,206 | B2 | 10/2009 | Atkins et al. | |
| 7,644,834 | B2 | 1/2010 | Castora et al. | |
| 7,665,491 | B2 | 2/2010 | Lampropoulos | |
| 7,967,147 | B2 | 6/2011 | Mimura | |
| 8,127,963 | B2 | 3/2012 | Gerson et al. | |
| 2007/0032764 | A1 | 2/2007 | Lampropoulos | |

OTHER PUBLICATIONS

Warner, Brandon J., "NonFinal OA", U.S. Appl. No. 13/559,285, filed Jul. 26, 2012; Mailed Apr. 11, 2013.

Warner, Brandon J., "Final OA", U.S. Appl. No. 13/559,285, filed Jul. 26, 2012; Mailed Jul. 31, 2013.

* cited by examiner

SPLASH-RETARDING FLUID COLLECTION SYSTEM

BACKGROUND

1. Technical Field

This invention relates generally to collection devices, and more particularly to fluid collection devices.

2. Background Art

Collection and disposal of fluids can be a complex process. While water can merely be poured down a drain, if the fluid is a toxic, hazardous, or environmentally unfriendly substance, such as a petroleum product or biological waste, care must be taken when collecting, containing, and disposing of such materials. For example, medical professionals, such as those working in a catheter or blood laboratory, must take care to properly dispose of fluids so as to avoid contaminating themselves or the environment with harmful materials.

It would be advantageous to have an improved container suitable for collection and disposal of fluids and other materials.

Figure 1:
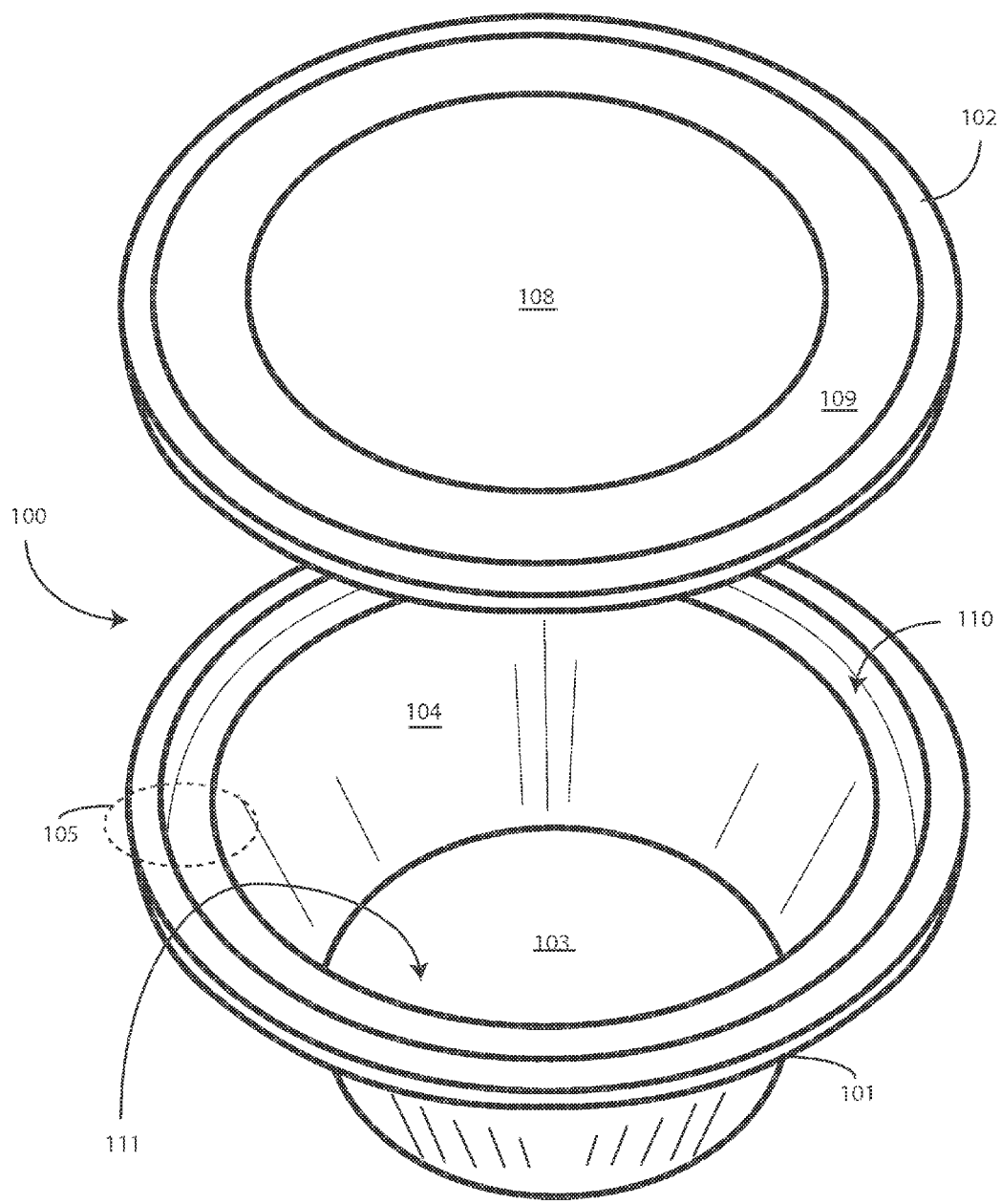
FIG. 1 illustrates one explanatory embodiment of a fluid collection container and lid configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A. The apparatus components and method steps described below have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

Proper collection and disposal of certain fluids and other materials is an important concern. For example, in the medical space, medical professionals pay special care to the appropriate disposition of blood, urine, tissue, and other biological materials that are obtained during medical procedures. The concern of proper collection and disposal stems from a desire to avoid contamination, possible infection, and exposure to such materials, as well as to abide by applicable rules and regulations concerning the disposal of such materials.

To this end, manufacturers have developed specialized fluid collection containers. The goal of such containers is to provide a container for handling and disposing fluids, and that is also more easily accommodated storage for both fluid and particulate waste. One such fluid collection container is disclosed in U.S. Pat. No. 6,053,314 to Pittman, entitled "Receptacle for contaminated wastes."

The '314 patent attempts to provide a device configured for ready receipt and safe disposal of liquid wastes, and also to minimize the likelihood of splatter of the liquid wastes when introducing liquid into the container. The '314 patent tries to accomplish this by providing a bowl and lid. The lid includes an opening through which liquids can be poured. The opening is sealed with a sheet of adhesive film that is permanently affixed at one end, and that can be peeled from the lid on the other end. A user peels back the adhesive film while liquids are poured into the opening. The adhesive film is then pressed back across the opening to seal the container.

Such a container suffers from a number of deficiencies. As a first example, the integrity of the seal between the adhesive film and the lid is dependent upon the user. A user in a hurry may insufficiently seal the adhesive film to the lid, thereby leaving an opening through which liquids may escape the container.

A second example is more problematic. Since the adhesive film is tacky on one side and permanently affixed to the lid, a user must hold the film in a folded back position while dispensing liquids through the opening in the lid. Many users find that the folded adhesive film difficult to manage. Consequently, rather than peeling the adhesive film back, they simply remove the entire lid, thereby defeating the purpose of having a specialized container in the first place.

Embodiments of the present invention provide a fluid collection container that offers many advantages over prior art designs. A first advantage is that the fluid entry into the container is large and wide. Rather than having a small aperture or specialized receptacle into which liquids are injected from a specialized device, like a syringe, embodiments of the present invention have large surfaces into which liquids may be injected, poured, or otherwise transferred. The large surface requires less accuracy in transferring liquids into the container when compared to prior art designs. Accordingly, a user may transfer fluids into the container more quickly and efficiently without any additional risk of spillage or contamination.

A second advantage is that embodiments of the present invention provide splash-retarding elements that prevent splash back of fluids during transfer to the container. In one or more embodiments, a mesh layer "gobbles" up liquid as it enters the container and eliminates or substantially prevents any splash back. Again, this feature allows a user to transfer fluids into the container more quickly and efficiently without any additional risk of spillage or contamination.

A third advantage is that liquids can be introduced into the container at a wide variety of angles. Prior art containers required users to inject fluids into containers using syringes or other medical devices. The syringes had to be oriented at just the proper angle to engage a specialized receptacle. Alternatively, small openings such as that found in the '314 patent required the user to hold the syringe at a particular angle. With embodiments described below, a user may inject, pour, or otherwise transfer fluids into a container at any of a variety of angles without concern of spillage or splash back. Other advantages will be readily apparent to those of ordinary skill in the art having the benefit of this disclosure.

Turning to FIG. 1, illustrated therein is one embodiment of a fluid collection container 100 configured in accordance with one or more embodiments of the present invention. The fluid collection container 100 comprises a vessel 101 and a lid 102 configured for attachment to the vessel 101. The vessel 101 is defined by a plurality of surfaces having contours configured to form a hollow container, similar to a bowl or cask, which can be used to hold liquid. The lid 102 is configured for selective attachment to the vessel 101 to form a closed fluid collection container. In one or more embodiments, when the lid 102 is attached to the vessel 101, a leak-proof seal is formed between vessel 101 and lid 102.

Both the vessel 101 and the lid 102 can be manufactured in a variety of ways. For example, in one embodiment the vessel 101 and the lid 102 can be manufactured from a thermoplastic material such as polypropylene by way of an injection molding process. The vessel 101 and lid 102 can alternatively be thermally formed on a mold from a soft thermoplastic, such as styrene or polystyrene. In another embodiment, the vessel 101 and lid 102 can be poured on a mold using a quick setting plastic, epoxy, or resin. Other methods of manufacture will be obvious to those of ordinary skill in the art having the benefit of this disclosure.

In one embodiment, the plurality of surfaces defining the vessel 101 includes a bottom surface 103 and a peripheral wall 104. For ease of illustration and efficiency of explanation, the explanatory vessel 101 shown in the figures has a bottom surface 103 that is round. The bottom surface 103 can be circular or oval, or alternatively can take other rounded shapes. However, it will be obvious to those of ordinary skill in the art having the benefit of this disclosure that embodiments of the invention are not so limited. The bottom surface 103 can be triangular, rectangular, or multisided polygonal as well. Where the bottom surface 103 is polygonal, the corresponding peripheral wall 104 may include orthogonal angles.

In the illustrative embodiment of FIG. 1, the peripheral wall 104 is round and tapers outward as it extends distally upward from the bottom surface 103. Such a taper can help the vessel 101 be extracted from a manufacturing tool. In this fashion, as shown in FIG. 1, the bottom surface 103 and the peripheral wall 104 are arranged in a frustoconical geometry.

In this embodiment, the peripheral wall 104 terminates in a contoured surface 105. The contoured surface 105 defines a stair-stepped flanged rim. The stair-stepped flanged rim will be shown and described in more detail with reference to FIG. 5 below.

In one embodiment, so as to be attachable to the vessel 101, the lid 102 includes an annular wall 106 disposed about a perimeter of the lid 102. The annular wall 106 defines a vessel receiving well 107 disposed beneath a central surface 108 of the lid 102 and within the annular wall 106. The central surface 108 spans an interior of the lid 102. In one embodiment, the central surface 108 is configured with an inclined ring 109 disposed about the central surface 108.

The bottom surface 103 and the peripheral wall 104 define an opening 110 disposed at an opposite end of the peripheral wall 104 from the bottom surface 103, and an interior 111 disposed between the opening 110, the bottom surface 103, and the peripheral wall 104. The opening 110 is configured to receive liquids and other substances into the vessel 101. Provided the vessel is in a generally upright position, with the bottom surface 103 disposed below the opening 110 in three-dimensional space, liquids and other substances transferred to the vessel 101 through the opening 110 will be retained in the interior 111 of the vessel 101.

Figure 2:
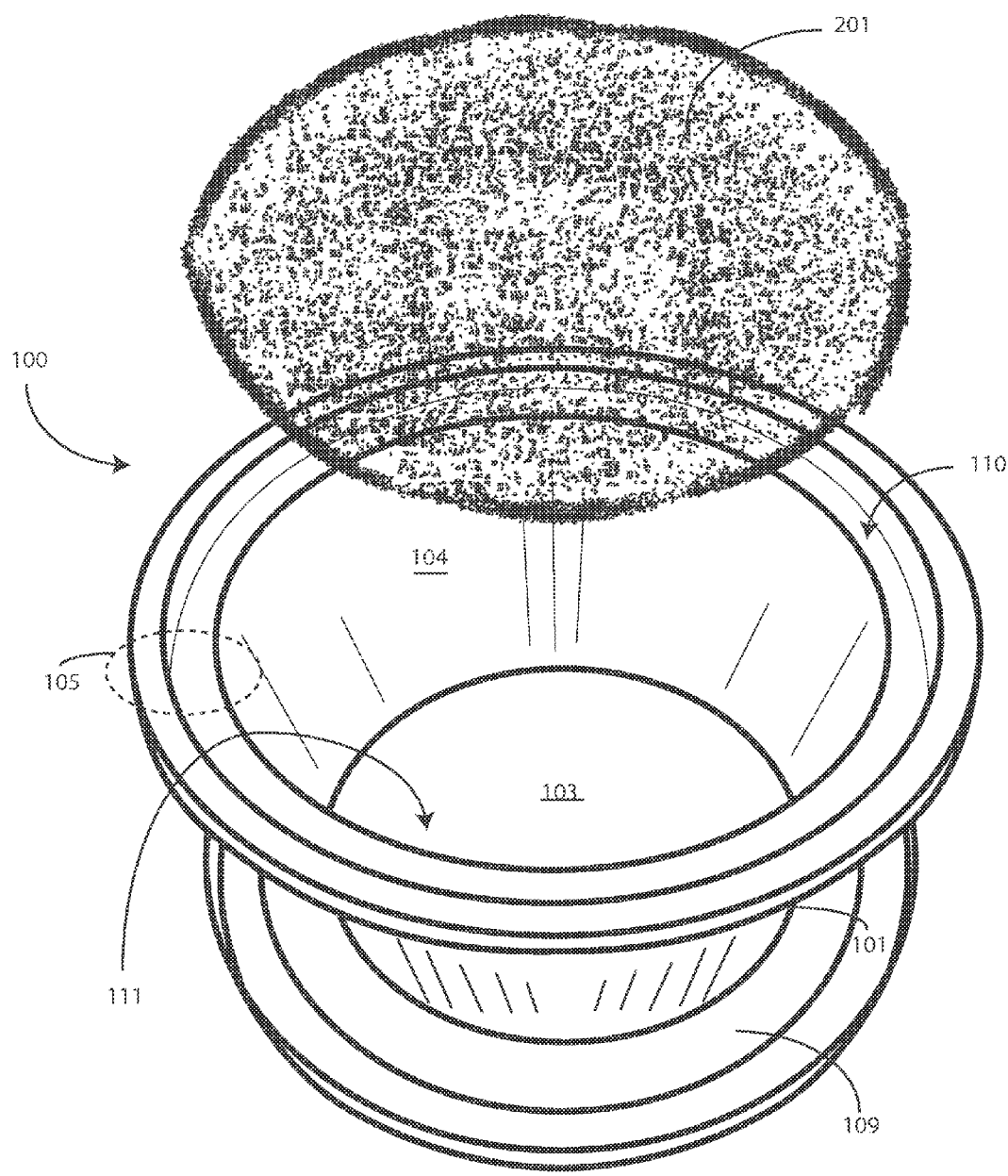
FIG. 2 illustrates an exploded view of a fluid collection container with mesh layer configured in accordance with one or more embodiments of the invention.

Turning now to FIG. 2, illustrated therein is the fluid collection container 100 of FIG. 1 with the lid 102 disposed beneath the vessel 101. Recall from FIG. 1 that in one embodiment an inclined ring 109 can be disposed about the central surface (108) of the lid 102. In this fashion, the central surface (108) can be configured to be substantially the same size as the bottom surface 103 of the vessel. Accordingly, when the vessel 101 is placed atop the lid 102 as shown in FIG. 2, the inclined ring 109 can serve as a retention device that centers the vessel 101 into the lid 102.

Figure 4:
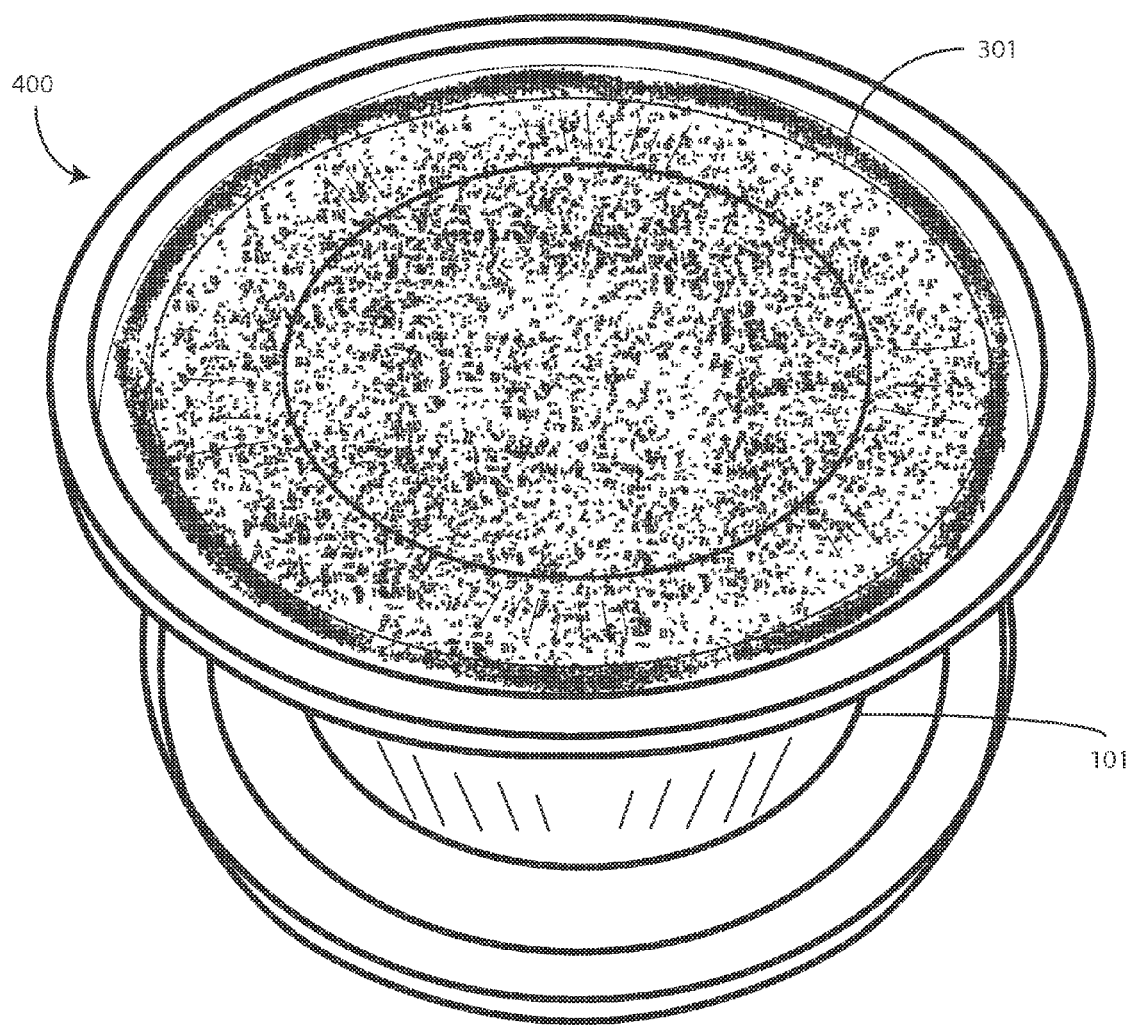
FIG. 4 illustrates one explanatory fluid collection container assembly configured in accordance with one or more embodiments of the invention.

FIG. 2 is presented in an exploded view with a mesh conduit layer 201 disposed above the fluid collection container 100. The mesh conduit layer 201 will be coupled to the vessel 101 as shown in FIG. 4, but is shown in an exploded view in FIG. 2.

The mesh conduit layer 201 is referred to as "conduit" in that it forms a channel for conveying water or other fluids. The mesh conduit layer 201 is a splash retarder in that it deflects liquid passing there through in directions other than that of incidence to prevent splash back. Said differently, the mesh conduit layer 201 disperses incident liquid to prevent is from splashing back toward the user.

In one embodiment, the mesh conduit layer 201 is manufactured from a woven material. For example, experimental testing has shown that a hydrophilic material such as cotton gauze manufactured with a loosely woven wave works well as the mesh conduit layer 201. In other embodiments, the mesh conduit layer is manufactured from a non-woven material. For example, in one embodiment a hydrophobic material such as spun glass—not unlike that used in inexpensive air filters used in ventilation systems—is used.

Other types of materials can be used as the mesh conduit layer 201 as well. For example, in one embodiment a fiber-spun non-woven material such as Thinsulate™ manufactured by 3M. Other examples of materials include spun cotton, spun glass, spun polyester, spun polyfibers, or spun nylon.

In one embodiment, "spunmelt" materials can be used as the mesh conduit layer 201. Spunmelt materials are non-woven materials that are extruded while the extrusion heads are vibrated to form a non-woven material layer. In another embodiment, the mesh conduit layer 201 is manufactured from spunbond-meltblown-spunbond material. Other materials can be used for the mesh conduit layer 201 include various woven, non-woven, hydroentangled materials, and/or combinations thereof, including spunlace, blends of polyester, polypropylene, polyethylene, urethane, and/or combinations thereof. The mesh conduit layer 201 can be manufactured using various other methods than those described above, including a spunbond metblown spundbond method, and a spunbond metblown metblown spundbond method.

In yet another embodiment, the mesh conduit layer 201 can be manufactured using a non-woven needle-punched process. In such a process, a non-woven bunch of interlocking fibers are fed into a needle punch machine. The non-woven bunch of interlocking fibers can be from a spunbond or carded web. Barbed felting needles then pass through the web of fibers, thereby causing one or more fibers to interlock. The materials and methods described above are illustrative only, as others will be readily apparent to those of ordinary skill in the art having the benefit of this disclosure.

In one embodiment, when the mesh conduit layer 201 is coupled to the vessel 101, it nests within the stair-stepped flanged rim of the contoured surface 105. When coupled in this manner, the mesh conduit layer 201 spans the opening 110 to enclose the interior 111 of the vessel 101. As the mesh conduit layer 201 is liquid permeable, despite enclosing the interior 111 of the vessel 101, liquid can be transferred to the interior by pouring or dispensing the liquid through the mesh conduit layer 201. As noted above, the mesh conduit layer 201 retards any splashing while the transfer occurs.

Figure 3:
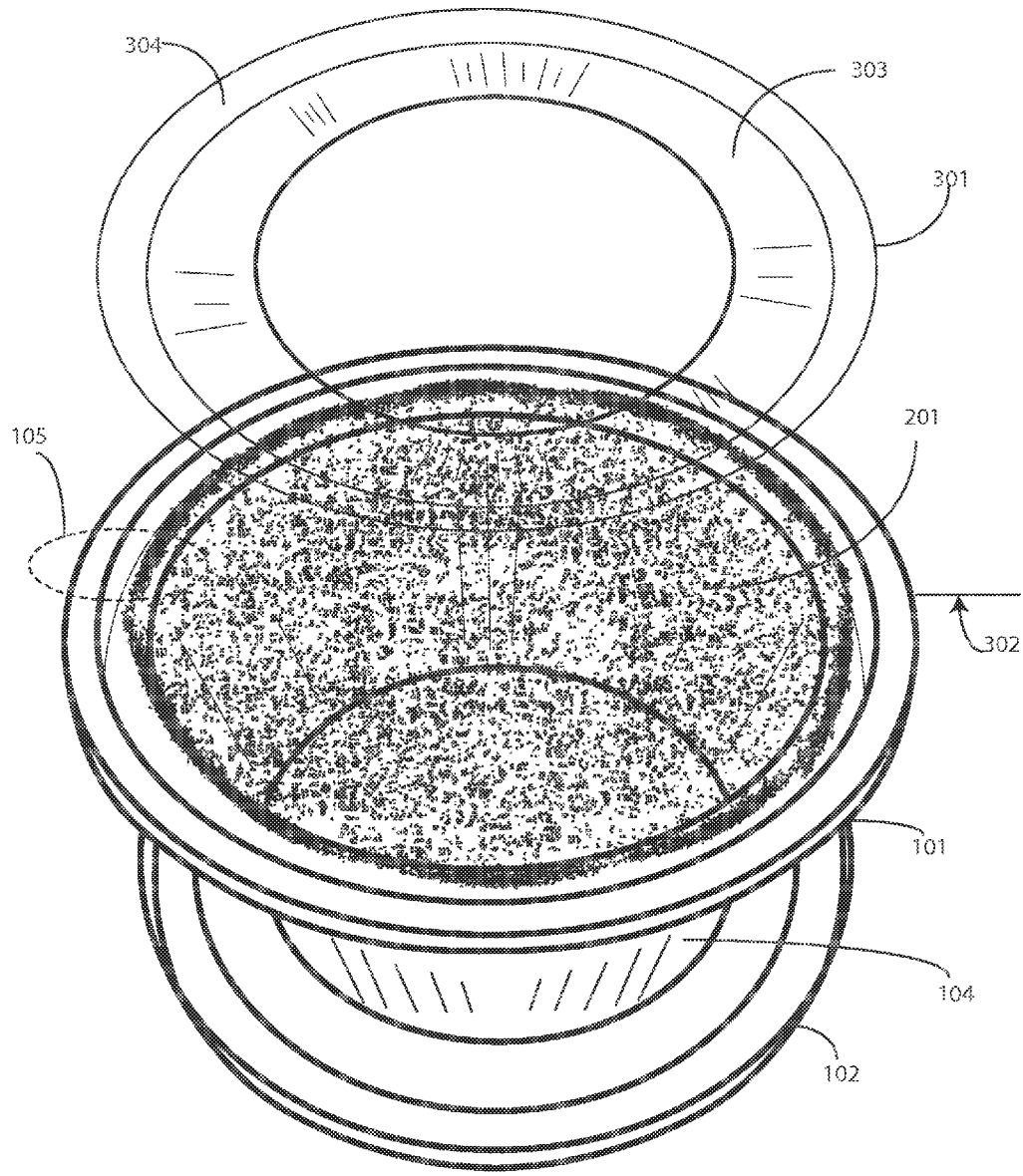
FIG. 3 illustrates an exploded view of a fluid collection container with mesh layer and retention ring configured in accordance with one or more embodiments of the invention.

Turning to FIG. 3, illustrated therein is one example of how the mesh conduit layer 201 can be attached to the vessel 101. As shown in FIG. 3, the mesh conduit layer 201 is disposed over the opening (110) of the vessel so as to span the opening (110) and enclose the interior of the vessel 101. The coupling means shown in FIG. 3 employs a retaining ring 301 that couples to the peripheral wall 104 atop the mesh conduit layer 201. Accordingly, when the retaining ring 301 is coupled to the vessel at the contoured surface 105, the mesh conduit layer 201 is disposed between the retaining ring 301 and the peripheral wall 104, thereby holding the mesh conduit layer 201 in place. The retaining ring 301 can be coupled to the contoured surface by an adhesive, thermal coupling, or other attachment methods.

In one embodiment, the retaining ring 301 is configured to seat within the stair-stepped flanged rim by coupling to the peripheral wall 104 at the contoured surface 105 such that it seats beneath an upper limit 302 of the vessel 101. When disposed in this position, the retaining ring 301 will not interfere with placement of the lid 102 atop the vessel 101. When the lid 102 is placed on the vessel 101 to create the closed vessel collection container, the lid 102 attaches over the mesh conduit layer 201, thereby sealing in any liquids in the interior (111) for convenient disposal. The retaining ring 301 of FIG. 3 can offer an additional advantage in that it can serve to retain liquids within the vessel 101 should it tip to the side slightly.

In the illustrative embodiment of FIG. 3, the retaining ring includes an inclined surface 303 that extends from a peripheral wall coupling member 304, which couples to the peripheral wall 104 at the contoured surface 105, towards the interior (111) of the vessel 101. The inclusion of the inclined surface 303 helps to direct liquids into the vessel 101. The retaining ring 301 is shown coupled to the vessel 101 as a completed assembly 400 in FIG. 4.

Figure 5:
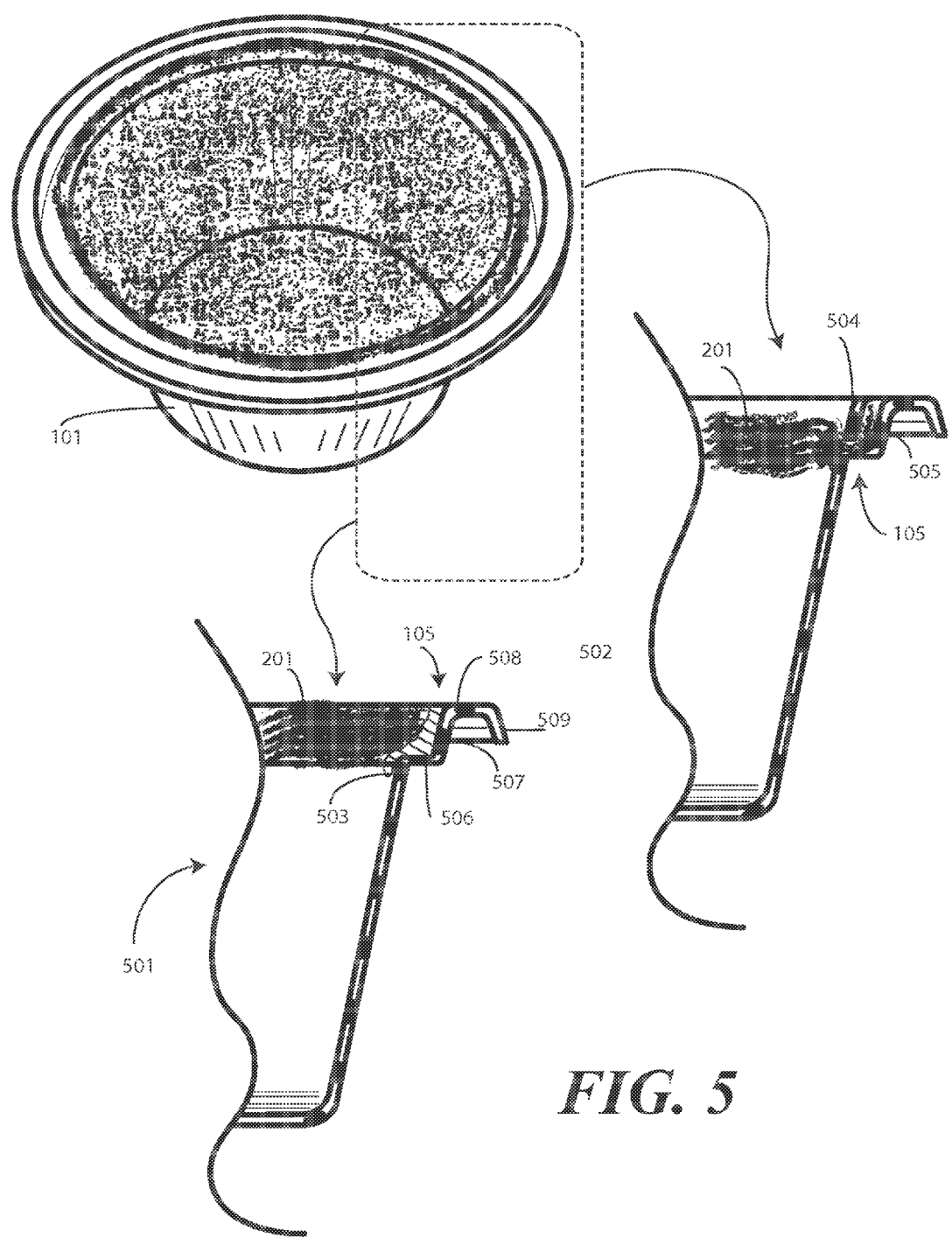
FIG. 5 illustrates one explanatory fluid collection container configured in accordance with one or more embodiments of the invention.

While the use of a retaining ring 301 is one example of a method of coupling the mesh conduit layer to the vessel 101, other methods that do not require a retaining ring 301 can also be used. Turning to FIG. 5, two such methods are shown.

In a first cut view 501, the mesh conduit layer 201 is adhesively coupled to the contoured surface 105 of the vessel 101. A layer of adhesive 503, which may be a silicone or hot melt adhesive, is disposed between the mesh conduit layer 201 and the contoured surface 105.

In a second cut view 502, the mesh conduit layer 201 has been insert molded into the contoured surface 105. This is accomplished by placing the mesh conduit layer 201 into a tool prior to injection molding a thermoplastic. As the thermoplastic passes about portions of the mesh conduit layer 201, it becomes attached to the contoured surface 105 with layers 504, 505 of material surrounding portions of the mesh conduit layer 201. These manufacturing methods are explanatory only, as other methods will be obvious to those of ordinary skill in the art having the benefit of this disclosure. For example, in one embodiment, both the vessel 101 and the mesh conduit layer 201 are manufactured from thermoplastics. In such an embodiment, a thermal process or heat bonding process can be used to weld the mesh conduit layer 201 to the vessel 101.

In addition to depicting alternative manufacturing methods, FIG. 5 illustrates one embodiment of the contoured surface 105 when configured as a stair-stepped flanged rim. As shown in FIG. 5, the stair-stepped flange rim includes a ledge 506, a tapered wall 507, a flange support 508, and a flange 509. In one embodiment, one or both of the flange support 508 and the flange 509 are flexible so as to positively engage the lid (102) to form the closed fluid collection container.

Figure 6:
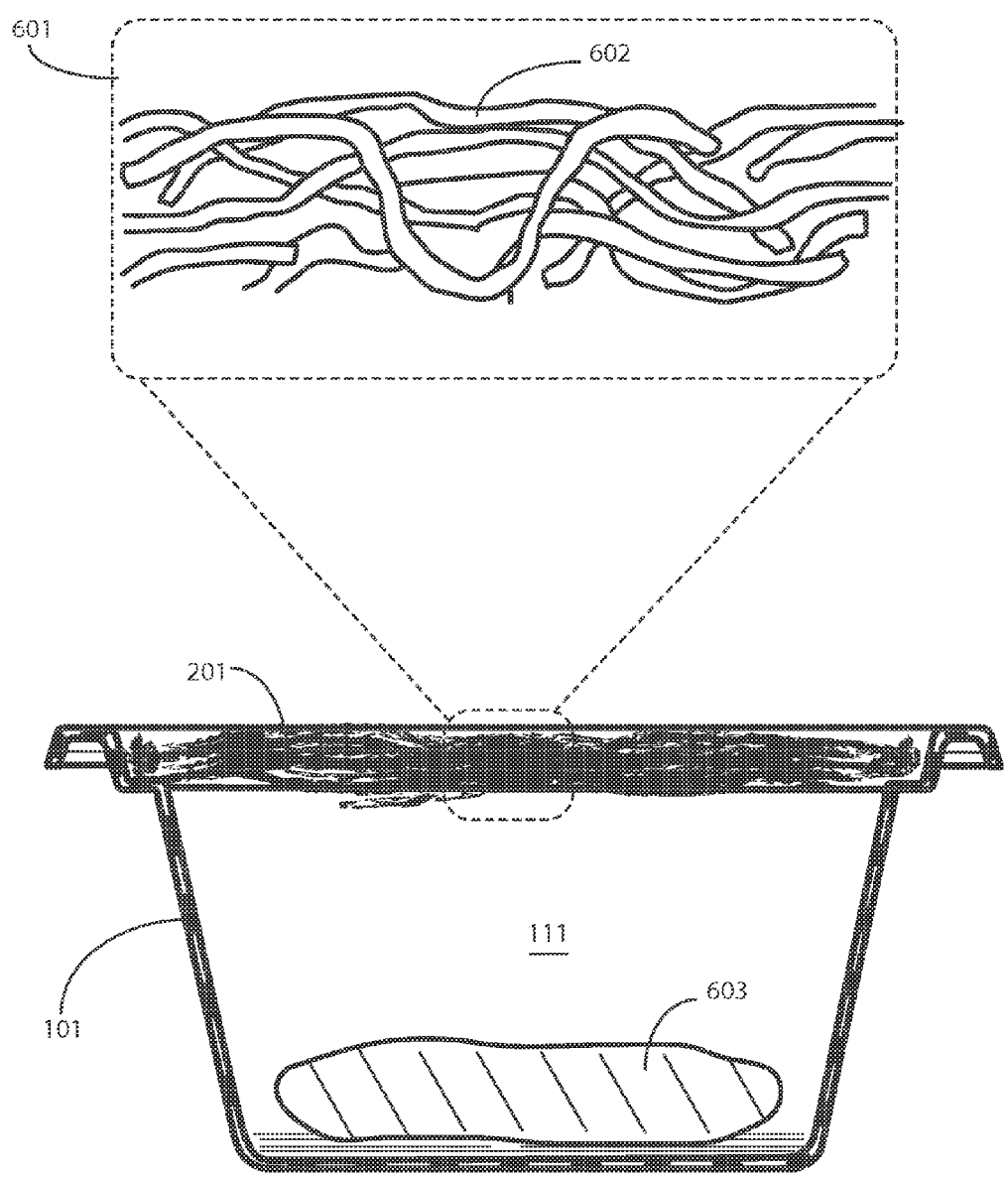
FIG. 6 illustrates alternate methods of coupling a mesh layer to a peripheral wall of one explanatory fluid collection container configured in accordance with one or more embodiments of the invention.

Turning now to FIG. 6, illustrated therein is an exploded view 601 of portions of one mesh conduit layer 201 configured in accordance with one or more embodiments of the invention. In this illustrative embodiment, the mesh conduit layer 201 is manufactured from hydrophobic, non-woven fibers 602. The hydrophobic, non-woven fibers 602 are spun glass that are liquid permeable and are configured to "gobble" liquids poured through them by slightly deflecting the liquid from their round cross-sectioned lengths to prevent splashing. In one embodiment, the fibers forming the mesh conduit layer are opaque and are intermingled with a density sufficient to prevent a user from seeing through the mesh conduit layer 201. Such an embodiment provides an extra aesthetic appeal in that the user need not constantly look at liquids or other materials disposed within the interior 111 of the vessel 101. Antimicrobial or toxin-neutralizing additives can be added to the mesh conduit layer 201 to treat liquids that pass through as well.

In the illustrative embodiment of FIG. 6, the vessel 101 has disposed within its interior 111 a cache 603 of coagulant material. The coagulant material is configured to cause liquids to change from a liquid state to a solid or semisolid state. For example, in a medical application the coagulant material can be a blood-specific coagulant configured to transform liquid blood into a gel to prevent spillage. In another embodiment, the coagulant can be a simple coagulant suitable for a variety of liquids. Such coagulants are routinely used as diaper gels in baby diapers.

As an alternative to coagulants, in one embodiment the cache 603 comprises a simple hydrophilic material such as gauze. When the gauze absorbs the inserted liquid, it becomes effectively coagulated by passing into the fibers of the gauze. Other absorbent materials can be substituted for the gauze as well.

Regardless of the material used, the cache 603 of coagulant material, where included, offers an advantage in that it counterbalances the vessel 101 when it becomes loaded. Said differently, once the cache 603 gets loaded, it lowers the center of gravity of the fluid collection container, which makes the vessel 101 harder to tip over. In many catheter procedures, a user will simply dump many containers of fluid into the vessel 101. A lower center of gravity allows this to be accomplished more quickly with less spillage.

Figure 7:
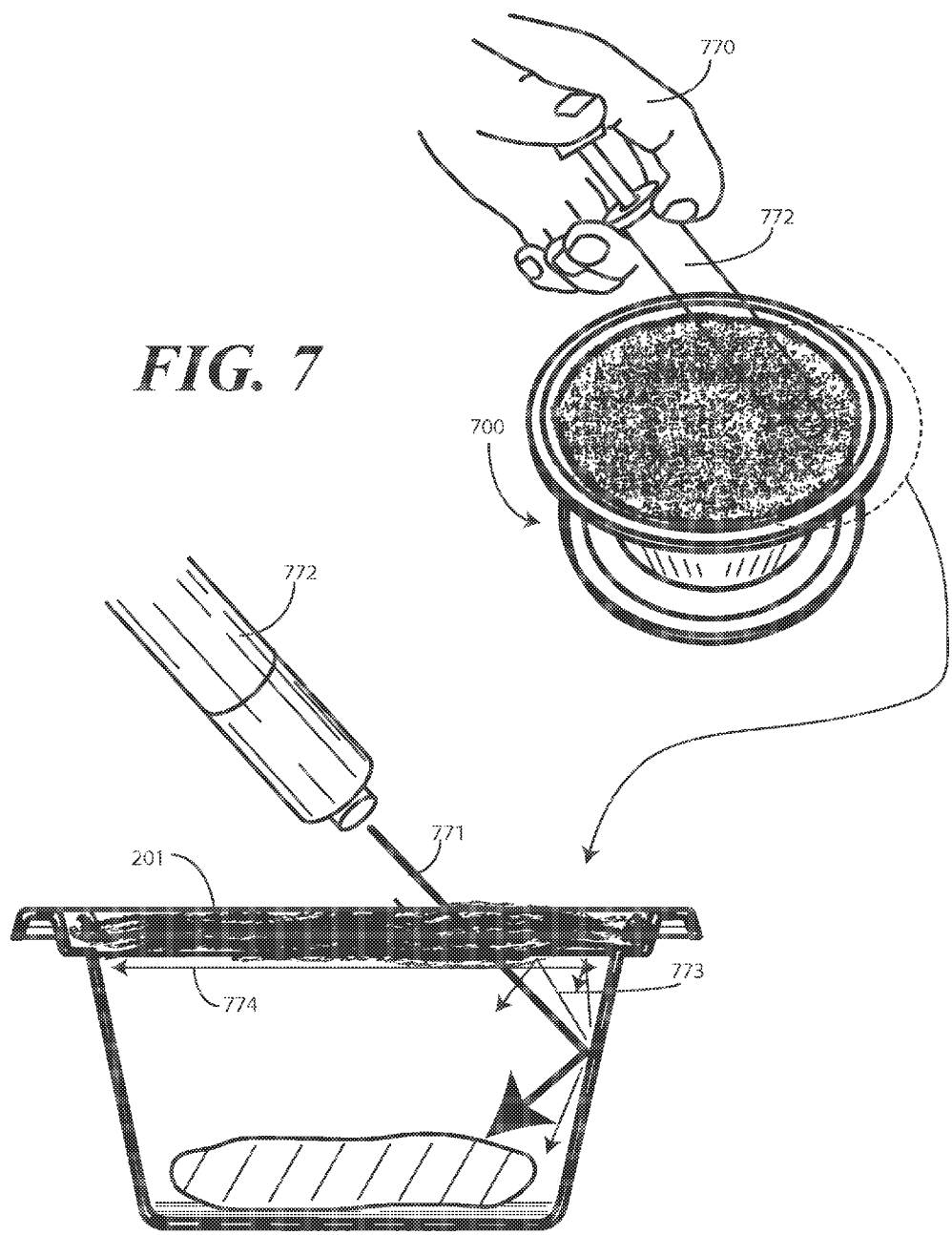
FIG. 7 illustrates splatter resistant properties of a fluid collection container configured in accordance with one or more embodiments of the invention.

Turning to FIG. 7, illustrated therein are some of the many benefits of using a fluid collection container 700 configured in accordance with embodiments of the invention. As shown, a user 770 is transferring liquid 771 through a mesh conduit layer 201 by way of a syringe 772. There is no need to engage the syringe 772 into special connectors or receptacles, nor is there any need to hold the syringe 772 with a particular orientation. To the contrary, the user 770 may simply hold the syringe 772 generally above the mesh conduit layer 201 and allow the liquid 771 to flow. The fibers of the mesh conduit layer 201 deflect portions 773 of the liquid that attempt to splash back toward the user 770.

While the user 770 is employing a syringe 772 in this illustrative embodiment, it should be noted that no specialized equipment is required to transfer the liquid 771 to the fluid collection container. The large surface area 774 of the mesh conduit layer 201 allows fluid from large containers to be simply dumped into the fluid collection container 700 without spillage.

Figure 8:
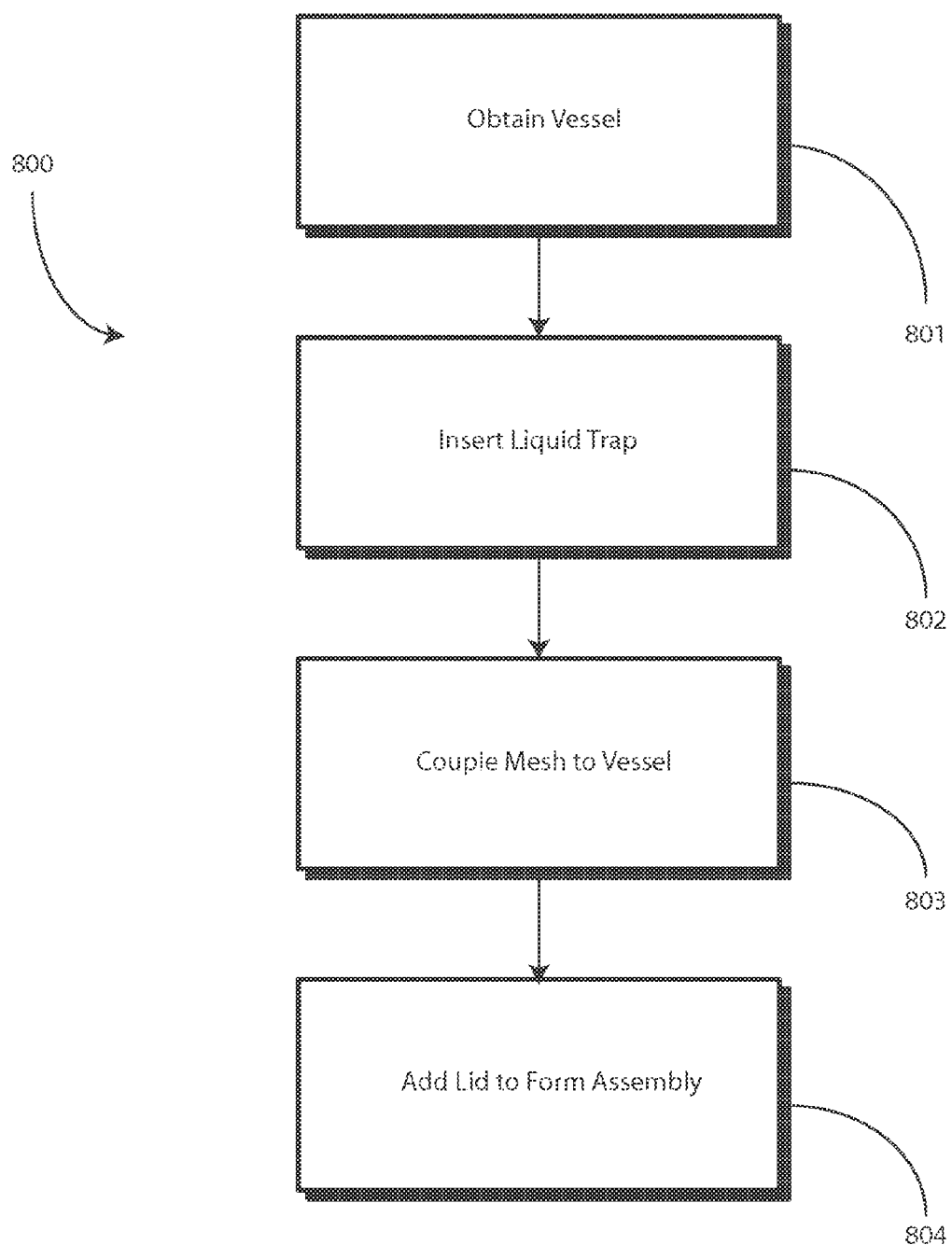
FIG. 8 illustrates one method of manufacturing a fluid collection container in accordance with one or more embodiments of the invention.

Turning to FIG. 8, illustrated therein is one method 800 of manufacturing a fluid collection container in accordance with one or more embodiments of the invention. The process steps have largely been described in conjunction with the apparatus drawings above, and so will only be cursorily discussed here.

At step 801, a manufacturer obtains a fluid collection vessel. As noted above, this can be manufactured from an injection molding process, procured from a third-party vendor, or manufactured by other methods. At step 802, the manufacturer optionally inserts a liquid trap into the interior of the vessel. In one embodiment, the liquid trap is a cache of coagulant, such as a gelling agent or an absorbent material.

At step 803, the manufacturer attaches a mesh spatter-retarding layer to the vessel. The mesh layer should be liquid permeable, and should span an opening of the vessel to enclose its interior. As noted above, various methods can be used to couple the mesh layer to the vessel, including adhesive attachment, thermal attachment, attachment by an insert molding process, or other methods.

At step 804, the manufacturer obtains or manufactures a lid. The lid can be packaged with the assembled vessel to form a fluid collection container ready for shipment to a user.

Figure 9:
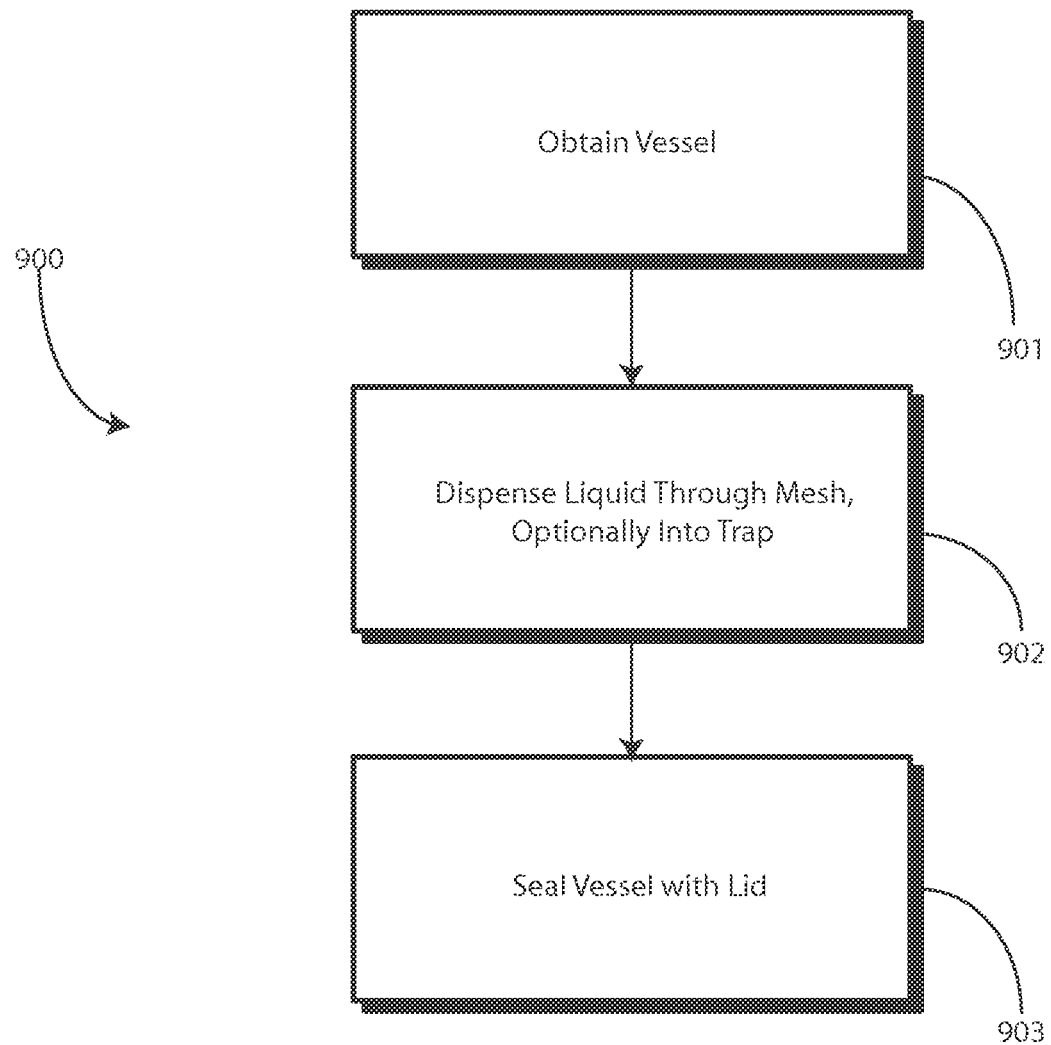
FIG. 9 illustrates one method of using a fluid collection container configured in accordance with one or more embodiments of the invention.

The user is then able to use the fluid collection container in accordance with the method 900 shown in FIG. 9. At step 901, the fluid collection container is obtained from the manufacturer. At step 902, the user transfers a liquid substance to the fluid collection container by passing the liquid substance through the liquid-permeable mesh layer disposed across an opening of the fluid collection container. At step 903, the user optionally attaches a lid to the fluid collection container to form a sealed fluid collection container.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A fluid collection container, comprising:
   a plurality of surfaces defining a vessel having a peripheral wall terminating to define a stair-stepped flanged rim to define an opening;
   a mesh conduit layer coupled to one or more of the plurality of surfaces by nesting within the stair-stepped flanged rim so as to span the opening and enclose an interior of the vessel; and
   a retaining ring separate from the vessel and coupled to the peripheral wall atop the mesh conduit layer and within the stair-stepped flanged rim such that the mesh conduit layer is disposed between the retaining ring and the stair-stepped flanged rim of the peripheral wall.

2. The fluid collection container of claim 1, further comprising a lid configured to attach to the vessel over the retaining ring and the mesh conduit layer to form a closed fluid collection container.

3. The fluid collection container of claim 1, wherein the plurality of surfaces comprise a bottom surface.

4. The fluid collection container of claim 3, wherein the bottom surface is polygonal.

5. The fluid collection container of claim 3, wherein the bottom surface and the peripheral wall are arranged in a frustoconical geometry.

6. The fluid collection container of claim 1, wherein the retaining ring comprises an inclined surface extending from the peripheral wall towards the interior of the vessel.

7. The fluid collection container of claim 3, wherein the mesh conduit layer is adhesively coupled to the peripheral wall.

8. The fluid collection container of claim 3, wherein the mesh conduit layer is thermally coupled to the peripheral wall.

9. The fluid collection container of claim 1, wherein the mesh conduit layer is coupled to the one or more of the plurality of surfaces by an insert molding process.

10. The fluid collection container of claim 1, wherein the mesh conduit layer comprises a hydrophobic material.

11. The fluid collection container of claim 1, wherein the mesh conduit layer comprises a hydrophilic material.

12. The fluid collection container of claim 1, wherein the mesh conduit layer comprises a woven material, a spun-woven material, or combinations thereof.

13. The fluid collection container of claim 1, wherein the mesh conduit layer comprises a non-woven material.

14. The fluid collection container of claim 13, wherein the non-woven material comprises one of spun material, spun-melt-spun material, spunbond material, spunlace material, or combinations thereof.

15. The fluid collection container of claim 1, further comprising a cache of coagulant disposed within the interior of the vessel.

16. The fluid collection container of claim 1, wherein the mesh layer is liquid permeable.

* * * * *